United States Patent [19]

Fyvie et al.

[11] Patent Number: 5,097,009
[45] Date of Patent: Mar. 17, 1992

[54] METHOD FOR MAKING CYCLIC OLIGOMERIC AROMATIC POLYCARBONATES FROM MONOCHLOROFORMATE

[75] Inventors: Thomas J. Fyvie, Schenectady; James M. Silva, Clifton Park, both of N.Y.

[73] Assignee: General Electric Company, Schenectady, N.Y.

[21] Appl. No.: 587,146

[22] Filed: Sep. 24, 1990

[51] Int. Cl.$^5$ .............................. C08G 64/26
[52] U.S. Cl. ................... 528/371; 528/196; 528/198; 528/199; 528/370
[58] Field of Search ............... 528/371, 198, 199, 196, 528/370

[56] References Cited

U.S. PATENT DOCUMENTS

| | | | |
|---|---|---|---|
| 3,193,528 | 7/1965 | Miller et al. | 260/47 |
| 4,638,077 | 1/1987 | Brunelle et al. | 558/281 |
| 4,644,053 | 2/1987 | Brunelle et al. | 528/371 |
| 4,737,573 | 4/1988 | Silva et al. | 528/371 |
| 4,814,429 | 3/1989 | Silva | 528/371 |

FOREIGN PATENT DOCUMENTS 1074398  7/1967  United Kingdom .

*Primary Examiner*—Harold D. Anderson
*Attorney, Agent, or Firm*—William A. Teoli; James C. Davis, Jr.; William H. Pittman

[57] ABSTRACT

A method for making cyclic polycarbonate oligomers is provided by converting oligomeric monochloroformate carbonates to the cyclic state. Improvements in materials usage, process control, and product characteristics are obtained.

6 Claims, No Drawings

METHOD FOR MAKING CYCLIC OLIGOMERIC AROMATIC POLYCARBONATES FROM MONOCHLOROFORMATE

CROSS REFERENCE TO RELATED APPLICATION

Reference is made to copending applications, serial number 519,979 and 519,980, both applications being filed concurrently on May 7, 1990 and assigned to the same assignee as the present invention.

BACKGROUND OF THE INVENTION

The present invention relates to a method for making cyclic oligomeric aromatic polycarbonates from monochloroformate oligomeric aromatic polycarbonate compositions.

Prior to the present invention, as shown by Brunelle and Shannon, U.S. Pat. Nos. 4,644,053 and 4,638,077, aromatic bischloroformates were prepared which were cyclized via a hydrolysis/condensation mechanism. Although valuable results are achieved utilizing the Brunelle and Shannon procedures, it has been found that during cyclization of the bischloroformate oligomers, about half of the chloroformate end groups are hydrolyzed to the corresponding aromatic hydroxyl endgroup before condensation takes place, i.e., the cyclization is hydrolysis limited. These chloroformate endgroups represent $COCl_2$ that is consumed during oligomer synthesis, but must be hydrolyzed to allow condensation to occur. Because of safety and environmental considerations, it is desirable to minimize the net $COCl_2$ requirements for cyclic carbonate synthesis. Hydrolysis of the bischloroformate consisting essentially of condensed carbonate units and included within the formula,

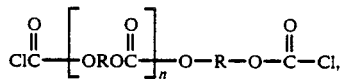
(1)

where R is a divalent $C_{(6-30)}$ aromatic organic radical, and n is an integer having a value of 0 to 40, requires 1–3 mol NaOH per mol of chloroformate end group hydrolyzed and generates by-products which include carbon dioxide, sodium carbonate, sodium bicarbonate and sodium chloride. These by-products require extra water to prevent salt precipitation. On the other hand, condensation of aromatic hydroxyl end groups with chloroformate end groups requires only 1 mol of base, per mol of chloroformate end group.

Further, since the slow step in the hydrolysis/condensation of bischloroformates during cyclization is hydrolysis of the chloroformate end group, chloroformates and amine/chloroformate complexes (acylammonium salts) are much more abundant in the mixture than aromatic hydroxyls. The acylammonium salt-terminated oligomers formed during the reactions between organic amine and the chloroformate end groups of the bischloroformate oligomer of formula (1), are interfacially active and can cause emulsification during cyclization. Experience has shown that during the period when the cyclization mixture is emulsified, it is often difficult to determine an accurate pH reading with a pH electrode. Inaccurate pH measurements can result in the addition of excessive alkali metal hydroxide to the cyclization mixture. In particular situations, product degradation manifested by ring opening to linear polymer and unreacted bisphenol A can occur. On the other hand, if insufficient alkali metal hydroxide is added to the cyclization mixture, undesirable levels of linear polycarbonate can be formed.

In copending application serial number 519,980, a method is shown for making oligomeric bisphenol monochloroformate polycarbonate oligomers. The bisphenol monochloroformate oligomers are comprised essentially of condensed carbonate units and are included within the formula,

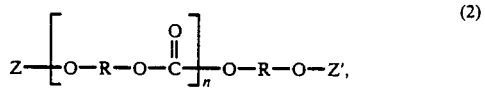
(2)

where R and n are as previously defined, Z and Z' are either H or

and the —OH and

terminal units of the bisphenol monochloroformate oligomers are present in an amount sufficient to provide an

ratio having a value of from about 0.9 to about 1.1, and preferably from 0.9 to 1.0. The overall monochloroformate oligomer mixture comprises bischloroformate oligomers (both ends chloroformate), monochloroformate oligomers (one hydroxyl end and one chloroformate end), and bishydroxy oligomers (both ends hydroxyl). The relative proportions of these oligomers in the bisphenol monochloroformate polycarbonate oligomer are substantially 1:2:1 for the bischloroformate, monochloroformate, and bishydroxyl.

As is shown in copending application serial no. 519,980, the aforementioned bisphenol monochloroformate polycarbonate oligomers can be made by phosgenating a mixture of bisphenol under interfacial conditions, where the mixture contains sufficient alkali metal hydroxide to provide a pH of up to about 11.2. As the phosgenation continues, the pH of the mixture continues to drop until a pH set point, for example 8, is reached. Additional make-up aqueous alkali metal hydroxide can be introduced at various rates, until a signal is shown indicating bisphenol monochloroformate oligomer formation whereupon termination of base and phosgene introduction can be effected. If a particular control system is used, for example "Control System A", aqueous alkali metal hydroxide can be introduced into the phosgenation mixture at a rate which substantially maintains the pH of the mixture at the pH set point during phosgenation until a sudden rise in base demand occurs. Alternatively, a "Control System B" can be used which restricts the aqueous alkali metal hydroxide introduction to a rate sufficient to provide a ratio of the rate of mols of aqueous alkali metal hydroxide introduction to the rate of mols of phosgene introduction having a value of about 2.0 to about 2.5. With Control System B, the pH of the phosgenation mixture is found to cycle around the pH set point until it is found to substantially stabilize and thereafter suddenly falls to at least 1 pH unit below its previous stabilized value. These signals identifying either a change in pH or base flow into the phosgenation mixture establish the threshold point of bisphenol monochloroformate polycarbonate oligomer formation and the point at which phosgenation and base introduction can be terminated.

In copending application serial number 519,979, a method is described for making end capped polycarbonates and bisphenol monochloroformate polycarbonate oligomers. In U.S. Pat. No. 4,616,077, Silva, incorporated herein by reference, there is shown a method for preparing cyclic polycarbonate oligomer from bischloroformate. However, the Silva procedure for making cyclics is subject to excessive emulsion generation and erratic pH measurement and control.

It would be desirable to effect the cyclization of chloroformate intermediates which are not hydrolysis limited and which do not require excess water to prevent salt precipitation. In addition, it also would be desirable to minimize the production of the emulsions during the formation of such cyclic oligomeric polycarbonates to allow for a more accurate pH reading to avoid the production of degradation products during the formation of such cyclic oligomeric polycarbonates as well as minimize the production of the linear polycarbonates.

SUMMARY OF THE INVENTION

The present invention is based on the discovery that bisphenol monochloroformate polycarbonate oligomers of formula (2) having an

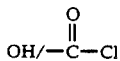

ratio of about 0.9 to about 1.1, can be converted to cyclic polycarbonate oligomers without generating sufficient emulsion to interfere with the maintenance of a pH range of from 10 to 12.5 during cyclic formation. The procedures used in converting the polycarbonate oligomers of formula (2) are adaptable to continuous operation utilizing an amine, such as triethylamine, and an alkali metal hydroxide in a tank reactor, such as a continuous stirred reactor in a mixed aqueous-organic system with agitation.

STATEMENT OF THE INVENTION

There is provided by the present invention, a method for making a polycarbonate composition comprising cyclic polycarbonate oligomers having structural units of the formula,

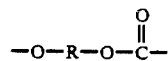

which comprises,
(1) simultaneously charging to a reactor,
 (A) a monochloroformate composition comprising bisphenol monochloroformate oligomer mixture comprising condensed carbonate units and included within formula 2,
 (B) at least one aliphatic or heterocyclic tertiary amine,
 (C) an aqueous alkali metal hydroxide solution and,
 (D) a substantially non-polar organic liquid which forms a two phase system with water, where reagent (A) is charged separately from reagents (B) and (C), (C) is introduced at a rate sufficient to maintain the pH of the reaction mixture at or near a pH setpoint in the range of between about 10 and about 12.5, which reaction mixture in said reactor is subjected to agitation at least sufficient to prevent segregation of the aqueous and organic liquid phases,
(2) allowing said reagents to react for a period of time sufficient to form cyclic oligomeric aromatic polycarbonate, and
(3) recovering said cyclic oligomeric aromatic polycarbonate, where R is as previously defined.

The bisphenol monochloroformate polycarbonate oligomer of formula (2) can be made in accordance with the procedure described in copending application Ser. No. 519,980, filed May 7, 1990. Accordingly, a reaction mixture is prepared by blending bisphenol with an organic solvent such as methylene chloride, water, and about 0.0–0.2 mol of alkali metal hydroxide, for example, sodium hydroxide, per mol of bisphenol. Sufficient alkali metal hydroxide can be utilized to raise the pH of the bisphenol reaction mixture, prior to phosgenation, to a value of up to about 11 resulting in the dissolution of some of the bisphenol into the aqueous phase. There also can be utilized from about 0 to 200 parts per million of a tertiary organic amine, such as triethylamine, relative to the weight of the organic solvent used in the formulation. Suitable organic solvents which can be used are for example, aliphatic hydrocarbons, such as hexane and heptane; chlorinated aliphatic hydrocarbons, such as methylene chloride, chloroform, carbon tetrachloride, dichloroethane, trichloroethane, tetrachloroethane, dichloropropane and 1,2-dichloroethylene; aromatic hydrocarbons, such as benzene, toluene and xylene; substituted aromatic hydrocarbons such as, chlorobenzene, o-dichlorobenzene, the various chlorotoluenes, nitrobenzene, and acetophenone; and carbon disulfide. The chlorinated aliphatic hydrocarbons, especially methylene chloride, are preferred.

Aqueous alkali, or alkaline earth metal hydroxide can be used to maintain the pH of the phosgenation mixture near the pH set point, which may be in the range of between about 3 to about 10.5. Some of the alkali metal or alkaline earth metal hydroxides, which can be employed are for example, sodium hydroxide, potassium hydroxide, and calcium hydroxide. Sodium and potassium hydroxides, and particularly sodium hydroxide is preferred. The concentration of the alkali hydroxide solution which is utilized is not critical and can be between about 0.2–19 M. Alkali concentrations of at least 5M are preferred.

The bisphenol polycarbonate monochloroformate oligomer forming reaction can be conducted in a wide variety of either semi-batch or continuous reactors. Such reactors are, for example, stirred tank reactors, which may be either semi-batch or continuous flow. Additional reactors which are included are recirculating loop continuous reactors.

The volume ratio of aqueous to organic phase during and at the termination of the phosgenation reaction can be in the range of about 0.2–1:1. Reaction temperatures can be in the range of between about 15–50° C. When the preferred organic liquid is utilized, such as methylene chloride, the reaction may be conducted at reflux which can be 35°–42° C. The reaction can be conducted at atmospheric pressure, although sub- or superatmospheric pressures may be employed if desired.

During phosgenation, the mixture is agitated, such as, by using a stirrer or other conventional equipment. The phosgenation rate can vary from between about 0.02–0.2 mol of phosgene, per mol of bisphenol per minute. During phosgenation, the pH is maintained at a desired value, frequently termed the pH set point, for example 8, which is chosen from the range of about 3 to about 10.5. A pH set point value at the low end of this range is desirable for making the bisphenol monochloroformate polycarbonate oligomer that can be utilized in making oligomeric cyclic mixtures; a pH set point value above about 8 is desirable for making oligomeric monochloroformate mixtures that will be utilized in making linear polymer.

One pH control method is to add aqueous alkali metal hydroxide to maintain the pH near the pH set point, at a maximum rate of about 2–2.5 mol NaOH/min per mol $COCl_2$/min (Control System B). For example, an on-/off pH control technique may be used. Aqueous alkali metal hydroxide is added whenever the pH of the system falls below the pH set point, at a rate of about 2.0 to about 2.5 mol NaOH/min per mol $COCl_2$/min. This on/off pH control technique can result in pH cycles in which the pH overshoots the set point by about 0.3–1 unit after the base pump is shut off and undershoots the set point by about 1–2 units after the base pump is turned on. After at least about 0.6 mol $COCl_2$ per mol bisphenol has been added, the pH of the system stabilizes at a level of about 0.1–0.5 pH units below the pH set point, during which time the base pump is on continuously. Termination of phosgene and alkali metal hydroxide introduction is effected at the point when a sudden decrease in the pH is detected after the pH of the mixture has substantially stabilized. A second pH control method (Control System A) is to add aqueous alkali metal hydroxide to maintain the pH near the pH set point, at a maximum rate of at least about 3 and preferably at least about 4 mol NaOH/min per mol $COCl_2$/min. This pH control technique can also result in fluctuating alkali metal hydroxide flow rates; however a moving average of the alkali metal hydroxide flow rate is substantially constant during the major part of the reaction, followed by a period of monotonically increasing flow rate. The period of the moving average is preferably about one alkali metal hydroxide flow rate cycle in duration. When the molar ratio of aqueous alkali metal hydroxide flow (moving average) to phosgene flow exceeds about 2.5–3.5, preferably about 3, the introduction of additional $COCl_2$ and aqueous alkali metal hydroxide can be discontinued.

Bisphenols or mixtures thereof which can be used in the practice of the present invention to make the bisphenol monochloroformate polycarbonate oligomers and the cyclic oligomeric aromatic polycarbonates derived therefrom, are for example, resorcinol
4-bromoresorcinol
hydroquinone
4,4'-dihydroxybiphenyl
1,6-dihydroxynaphthalene
2,6-dihydroxynaphthalene
bis(4-hydroxypenyl)methane
bis(4-hydroxyphenyl)diphenylmethane
bis(4-hydroxyphenyl)-1-naphthylmethane
1,1-bis(4-hydroxyphenyl)ethane
1,2-bis(4-hydroxyphenyl)ethane
1,1-bis(4-hydroxyphenyl)-1-phenylethane
2,2-bis(4-hydroxyphenyl)propane ("bisphenol A")
2-(4-hydroxyphenyl)-2-)3-hydroxyphenyl)propane
2,2-bis(4-hydroxyphenyl)butane
1,1-bis(4-hydroxyphenyl)isobutane
1,1-bis(4-hydroxyphenyl)cyclohexane
1,1-bis(4-hydroxyphenyl)cyclododecane
trans-2,3-bis(4-hydroxyphenyl)-2-butene
2,2-bis(4-hydroxyphenyl)adamantane
α,α'-bis(4-hydroxyphenyl)toluene
bis(4-hydroxyphenyl)acetonitrile
2,2-bis(3-methyl-4-hydroxyphenyl)propane
2,2-bis(3-ethyl-4-hydroxyphenyl)propane
2,2-bis(3-n-propyl-4-hydroxyphenyl)propane
2,2-bis(3-isopropyl-4-hydroxyphenyl)propane
2,2-bis(3-sec-butyl-4-hydroxyphenyl)propane
- 2,2-bis(3-t-butyl-4-hydroxyphenyl)propane2,2-Bis(3-cyclohexyl-4-hydroxyphenyl) propane
2,2-bis(3-allyl-4-hydroxyphenyl)propane 2,2-bis(3-methoxy-4-hydroxyphenyl)propane
2,2-bis(3,5-dimethyl-4-hydroxyphenyl)propane
2,2-bis(2,3,5,6-tetramethyl-4-hydroxyphenyl)propane
2,2-bis(3-5-dichloro-4-hydroxyphenyl)propane
2,2-bis(3,5-dibromo-4-hydroxyphenyl)propane
2,2-bis(2,6-dibromo-3,5-dimethyl-4-hydroxyphenyl)propane
α,α'-bis(4-hydroxyphenyl)toluene
α,α,α', α'-Tetramethyl-α,α'-bis(4-hydroxyphenyl)-p-xylene
2,2-bis(4-hydroxyphenyl)hexafluoropropane
1,1-dichloro-2,2-bis(4-hydroxyphenyl)ethylene
1,1-dibromo-2,2-bis(4-hydroxyphenyl)ethylene
1,1-dichloro-2,2-bis(5-phenoxy-4-hydroxyphenyl)ethylene
4,4'-dihydroxybenzophenone
3,3-bis(4-hydroxyphenyl)-2-butanone
1,6-bis(4-hydroxyphenyl)-1,6-hexanedione
ethylene glycol bis(4-hydroxyphenyl)ether
bis(4-hydroxyphenyl)ether
bis(4-hydroxyphenyl)sulfide
bis(4-hydroxyphenyl)sulfoxide
bis(4-hydroxyphenyl)sulfone
bis(3,5-dimethyl-4-hydroxyphenyl)sulfone
9,9-bis(4-hydroxyphenyl)fluorene
2,7-dihydroxypyrene
6,6'-dihydroxy-3,3,3',3'-tetramethylspiro (bis)indane("spirobiindane bisphenol")
3,3-bis(4-hydroxyphenyl)phthalide
2,6-dihydroxydibenzo-p-dioxin
2,6-dihydroxythianthrene
2,7-dihydroxyphenoxathiin
2,7-dihydroxy-9,10-dimethylphenazine
3,6-dihydroxydibenzofuran
3,6-dihydroxydibenzothiophene
2,7-dihydroxycarbazole In the practice of the present invention, the cyclic oligomeric aromatic polycarbonates are prepared by simultaneously charging to a tank reactor, bisphenol monochloroformate polycarbonate oligomer (A), the aliphatic or heterocyclic tertiary amine (B), the alkali metal hydroxide solution (C), and the non-polar organic liquid (D). To avoid premature reaction, it is necessary to charge reagent A separately from reagents B and C. Most often, reagent A is combined with reagent D, the solvent, and the resulting solution is charged. Reagent B may also be charged as a solution in reagent D. Reagents B and C may be charged separately or in combination.

The conditions in the tank reactor are maintained so as to insure agitation (preferably by stirring) of the reaction mixture to a degree at least sufficient to prevent segregation of the aqueous and organic liquid phases. Less effective agitation conditions decrease the yield of cyclic oligomer as a result of incomplete contact between the reagents, while agitation which is too rapid causes an increase in linears at the expense of cyclics.

It will be apparent to those skilled in the art that a number of parameters can affect the conditions of agitation. Among these are the design and location of charging means for the reagents; the design, location and speed of operation of agitating means; and the presence or absence and design of agitation facilitating means such as baffles in the reactor. It is generally preferred to introduce all reagents under the surface of the reaction mixture in the tank reactor. Other parameters can readily be adjusted by those skilled in the art with minimum experimentation so as to provide the required agitation conditions.

The reaction between the above-described reagents is allowed to proceed for a period of time sufficient to produce the desired cyclic polycarbonate oligomers. For example, the residence time in a continuous stirred tank reactor (hereinafter "CSTR") is usually in the range of about 6-30 minutes, especially about 8-16 and preferably about 8-12 minutes. It has been found that reaction is essentially complete irrespective of residence time. However, at shorter residence times the amount of linears in the product sharply increases, while at residence times greater than about 20 minutes, hydrolysis of the bischloroformate portion of reagent (A) and/or cyclic oligomer product by the aqueous phase may occur, also leading to an increase in formation of linears.

For semi-batch operation, the rate of introduction of reagent (A) influences the yield of cyclic oligomers. The range of addition rate is 0.5 mol structural units per liter total organic phase per 15-90 minutes; the preferred range is 0.5 mol structural units per liter total organic phase per 20-60 minutes.

Reaction temperature, considered in isolation, is not a crucial factor in the practice of the invention. There is seldom an advantage in operating below about 20° C., since the reaction rate may then be undesirably low. When the reaction is conducted at or near atmospheric pressure, temperatures above 100° C. are seldom warranted, in part because of the high energy input required. Under most circumstances, a temperature no higher than about 50° C. is appropriate. It is within the scope of the invention, but seldom advantageous, to operate above or below atmospheric pressure. However, higher temperatures may be employed if the method is conducted at elevated pressures.

In two respects, the temperature effect may be material. The first is the increasing disorder in the system as the temperature approaches reflux, and further increasing disorder as the intensity of reflux increases. Such an increase in disorder should generally be accompanied by a decrease in externally provided agitation, so as to maintain the previously described conditions of agitation.

The second consideration is the effect of temperature on residence time for continuous reactors. For example, the boiling point of methylene chloride is about 40° C. As that temperature is approached closely, there is a sharp increase in the volume of vapor in the system. Much vapor is present as bubbles in the liquid phase, decreasing the liquid volume in the reaction vessel. When a CSTR is employed, the residence time decreases in inverse proportion to the volume of vapor contained as bubbles in the liquid phase. This is one factor in the importance of reaction temperature, especially when a low boiling solvent such as methylene chloride is employed.

Balancing these factors, it is frequently found advantageous to operate at a reaction temperature from about 20° C. to reflux. Temperatures in the range of about 25°-40° C. are often convenient.

Another factor of some importance when a low boiling solvent is used is the avoidance of solvent loss by volatilization. Solvent loss, with a resulting decrease in the volume of the organic phase, can cause reproducibility problems if inefficient condensing means are utilized. It may be advisable under these circumstances to employ cooling temperatures as low as 0° C. in one or more condensers. It may also be advisable to provide a liquid seal on any CSTR outlet port, as described hereinafter.

The yield of low molecular weight cyclic oligomers is generally dependent to some extent on the proportion of reagent B, in terms of concentration of B in mols per liter of reagent D. The concentration of reagent B is most often in the range of about 0.02-0.50 and preferably about 0.03-0.15 mol per liter of organic phase (i.e., all constituents except aqueous phase) in the reaction mixture.

The yield of cyclic oligomers is also influenced by the product concentration. Thus, for either semi-batch or CSTR operation, the preferred range of product concentration is 0.1 to 1.5 mol structural units per liter organic phase. 5 For the most part, other reaction conditions do not have as pronounced an effect on the composition of product as do the degree of agitation and residence time. The volume ratio of aqueous to organic phase is ordinarily in the range of about 0.05-1.0:1.

After the desired residence time or semi-batch reaction time the desired cyclic oligomer product is recovered, typically by quenching of the reaction mixture by contact with an excess of water or, preferably, a dilute aqueous acid solution. The product is thus obtained as a solution in reagent D, from which it may be separated by conventional means such as evaporation of solvent or precipitation by addition of a non-solvent. At this stage it is also possible to separate from the cyclic oligomers any linears or other impurities. The degree of sophistication of recovery will depend on such variables as the intended end use of the cyclic oligomer composition.

The method of this invention is adaptable to both semi-batch and continuous operation. Semi-batch operation is often most conveniently effected by first charging the reaction vessel with a portion of reagent D and optionally also of reagents B and C, and subsequently adding reagent A and the remainder of reagents B, C and D.

One advantage of the invention is its adaptability to continuous operation. For this purpose, a CSTR may be employed. In addition to conventional reagent introduction means, agitation means and optional heating and/or cooling and agitation facilitating means, such a reactor has an outlet port for the continuous removal of product. The outlet port is typically located on the perimeter of the reactor, at a distance from the bottom sufficient to provide the desired liquid holdup and residence time in the reactor. To avoid loss of volatile solvents by vaporization, it is frequently preferred for the outlet port to have a suitable liquid seal, which may be provided by an inverted U-shaped bend or a similarly disposed right angle bend.

When a CSTR of the above-described design is used, there may be an interrelation between stirring rate and residence time. This is particularly true when the organic liquid employed is denser than water, as is true of methylene chloride and most other halogenated hydrocarbons. Under these conditions, if the stirring rate is too rapid a liquid-liquid centrifuge effect may cause premature discharge of a portion of the organic phase. It will be apparent that such premature discharge can be avoided by decreasing the stirring rate of the reaction mixture. This is another important reason why it is critical that the stirring rate not be excessive.

In order that those skilled in the art will be better able to practice the present invention, the following example is given by way of illustration and not by way of limitation. All parts are by weight unless otherwise indicated.

EXAMPLE 1

A mixture of 186 grams (0.81 mols) of bisphenol A, 550 ml of methylene chloride, 250 ml of $H_2O$, and 5 ml of 50 weight % NaOH was phosgenated. The phogenation reaction was run at a temperature in the range of between 15–39° C. and at pH set points of between 5 to 8.2. A pH control system was used which provided an NaOH flow rate of 6.7 ml/min of 50 weight % NaOH (19 M) when the pH was below the pH set point and zero otherwise, while the phosgenation rate was set at about 5.8 grams per min. Five phosgenation reactions ( Table I: Phos-1-5) were run where Phos-1 and Phos-2 were initially at room temperature and then allowed to reach reflux. The balance of the phosgenation reactions were run at temperatures between 15 to 27° C. During the phosgenations, the pH, which was monitored, initially cycled about the pH set point. The pH then stabilized to a value just below the pH set point. The pH suddenly fell to a value at least 1 pH unit below the previously stabilized value. For reactions Phos-1-5, phosgenation was terminated 30–60 seconds after the sudden drop in pH. After the phosgenations were completed, samples were taken immediately and analyzed by HPLC. The reactor was purged with nitrogen under pH control for 5-10 minutes to hydrolyze residual phosgene. The phases were allowed to separate and the organic phase recovered. The products of Phos-1-5 were found to be predominantly monochloroformate species (46-66% of the structural units) and the molar ratios of hydroxyl to chloroformate end groups were found to be approximately 1 by HPLC analysis.

An additional phosgenation (Phos-6) was run where a temperature of 15-18° C. and a reaction pH of 4 was maintained. In addition, the phosgenation rate of Phos-1-5 was used to deliver a portion of 2 mols of phosgene per mol of bisphenol A. In the product of Phos-6, 86% of the structural units were bischloroformates and only 9% of the structural units were monochloroformates. The following results were obtained:

TABLE I

| Phosgenation Conditions and Product: | | | | | | |
|---|---|---|---|---|---|---|
| Phosgenation Reactions | | | | | | |
| | Phos-1 | Phos-2 | Phos-3 | Phos-4 | Phos-5 | Phos-6* |
| Phosgenation Conditions | | | | | | |
| Temp., C. | 39 | 39 | 15–20 | 27 | 27 | 15–18 |
| Reaction pH | 8.2 | 5 | 5 | 5 | 5 | 4 |
| mol $COCl_2$/mol BPA | 1.08 | 1.31 | 1.52 | 1.46 | 1.86 | 2 |
| Phosgenation Product** | | | | | | |
| 1-MCF | 8.42 | 23.86 | 24.18 | 38.44 | 40.50 | 2.46 |
| 2-MCF | 11.20 | 13.44 | 12.94 | 14.84 | 13.20 | 2.77 |
| 3-MCF | 8.87 | 7.72 | 7.02 | 6.41 | 4.80 | 1.02 |
| 4-MCF | 7.15 | 7.19 | 4.33 | 3.75 | 1.90 | 0.55 |
| 5-MCF | 5.11 | 3.11 | 2.36 | 1.56 | 0.80 | 1.06 |
| 6-MCF | 3.12 | 1.79 | 0.42 | 0.78 | 0.30 | 0.56 |
| 7-MCF | 1.84 | 1.01 | 0.67 | 0.00 | 0.00 | 0.24 |
| 8-MCF | 0.00 | 0.00 | 0.00 | 0.00 | 0.00 | 0.00 |
| 1-BCF | 6.18 | 10.52 | 18.48 | 12.03 | 15.00 | 49.12 |
| 2-BCF | 4.90 | 6.05 | 10.01 | 8.28 | 8.60 | 18.23 |
| 3-BCF | 3.27 | 3.08 | 5.78 | 3.75 | 3.30 | 9.58 |
| 4-BCF | 2.45 | 1.98 | 2.99 | 1.56 | 1.30 | 4.22 |
| 5-BCF | 1.32 | 0.98 | 0.77 | 0.63 | 0.50 | 2.26 |
| 6-BCF | 0.71 | 0.38 | 1.00 | 0.00 | 0.00 | 1.14 |
| 7-BCF | 0.00 | 0.00 | 0.00 | 0.00 | 0.00 | 0.54 |
| 8-BCF | 0.00 | 0.00 | 0.00 | 0.00 | 0.00 | 0.44 |
| BPA | 0.55 | 0.95 | 1.36 | 2.97 | 5.60 | 5.81 |
| L-2 | 4.13 | 5.43 | 2.68 | 2.34 | 3.10 | 0.00 |
| L-3 | 6.00 | 4.83 | 2.01 | 1.56 | 0.60 | 0.00 |
| L-4 | 4.76 | 2.78 | 1.09 | 0.63 | 0.30 | 0.00 |
| L-5 | 3.69 | 0.00 | 0.00 | 0.47 | 0.20 | 0.00 |
| L-6 | 2.60 | 1.18 | 0.29 | 0.00 | 0.00 | 0.00 |
| L-7 | 1.71 | 0.87 | 0.00 | 0.00 | 0.00 | 0.00 |
| L-8 | 1.25 | 0.38 | 0.00 | 0.00 | 0.00 | 0.00 |
| Higher Oligomers, % | 10.77 | 2.47 | 1.62 | 0.00 | 0.00 | 0.00 |
| Total MCF | 45.71 | 58.12 | 51.92 | 65.78 | 61.50 | 8.66 |
| Total BCF | 18.83 | 22.99 | 39.03 | 26.25 | 28.70 | 85.53 |
| Total Linears | 24.69 | 16.42 | 7.43 | 7.97 | 9.80 | 5.81 |

*Comparative BCF Phosgenation and Product
**Mol structuraal units as specific oligomer/100 mol structural units The above results show that Phos-1-5 consists of a major amount of monochloroformate species while Phos-6 consists of a major amount of bischloroformate species.

The above monochloroformate (MCF) and bischloroformate (BCF) oligomers were then cyclized. The respective oligomers (CYC-1-6) were cyclized in a semi-batch reactor utilizing a mixture of methylene chloride, water, 25 weight % NaOH solution, and triethylamine. A reaction time of from 10-120 minutes was employed utilizing a stir rate of from 275-600 rpm, a reaction pH of from 8.5-12 and a temperature of 35° C. In instances where the monochloroformate oligomers were cyclized, the pH was controlled by adding a 25 weight % NaOH solution with a pump that was controlled with a pH controller. When the pH (measured by a glass pH electrode) exceeded the set point of 11, the pump shut off and the when the pH fell below the pH set point the pump was activated. As a result, the cyclizations of the MCF solutions, the pH measurement by the glass pH electrode was always reliable, and responsive and accurate within 0.5 to 1.0 pH unit.

In contrast, the pH electrode readings during the cyclization of the bischloroformates (BCF) were not feasible, since emulsions were formed which interfered with the use of the pH electrode. In order to avoid difficulty, samples were taken frequently during bischloroformate cyclization reactions. Manual measurements with pH paper (CYC-6A) were used in order to determine whether to continue or stop the addition of the 25 weight % NaOH solution. Another cyclization of the bischloroformate oligomer mixture (CYC-6B) was attempted in which samples were taken less frequently than in CYC-6A. Manual measurements with pH paper were again used in order to determine whether to continue or stop the addition of 25 weight % NaOH solution. Table 2 below shows in detail the cyclization conditions and the cyclization products recovered from the cyclization of the monochloroformates and bischloroformates:

nitrogen into a salt bath at 300° C. for 2 minutes. Molecular weights by GPC of 244,000 (Mw) and 89,000 (Mn) were obtained.

Although the above example is directed to only a few of the very many variables which can be utilized in the practice of method of the present invention, it should be understood that the present invention is directed to a much broader variety of cyclic polycarbonates and methods for making.

What is claimed is:

1. A method for making a polycarbonate composition comprising cyclic polycarbonate oligomers having structural units of the formula,

TABLE II

| | Cyclization Conditions and Product | | | | | | | | | |
|---|---|---|---|---|---|---|---|---|---|---|
| | Cyclization Reaction | | | | | | | | | |
| | CYC-1 | CYC-2 | CYC-3 | CYC-4A | CYC-4B | CYC-4C | CYC-4D | CYC-5 | CYC-6A* | CYC-6B* |
| Cyclization Conditions | | | | | | | | | | |
| Rxn Time, min | 20 | 30 | 30 | 10 | 10 | 10 | 10 | 120 | 10 | 30 |
| Stir Rate, rpm | 275 | 275 | 275 | 275 | 400 | 400 | 600 | 275 | 275 | 275 |
| Reaction pH | 12–13 | 11–12 | 12–13 | 11–12 | 10–12 | 10–12 | 10–12 | 10–12 | 9–12 | 8.5–12 |
| Temp, C. | 25 | 35 | 35 | 35 | 35 | 35 | 35 | 35 | 35 | 35 |
| Initial Reactor Charge: | | | | | | | | | | |
| CH2Cl2, ml | 108 | 135 | 135 | 74 | 74 | 74 | 74 | 51.5 | 74 | 56 |
| H2O, ml | 15 | 19 | 19 | 10 | 5 | 5 | 5 | 10 | 5 | 10 |
| NaOH, ml (25% wt) | 1.5 | 1.2 | 0.5 | 0.5 | 2.3 | 2.3 | 2.2 | 0.5 | 1.2 | 0.2 |
| Et3N, ml | 1.3 | 1.2 | 1.6 | 1.13 | 0.85 | 0.57 | 0.85 | 0.62 | 1.13 | 0.68 |
| Reactants Added Over Time | | | | | | | | | | |
| CF Rectant | Phos-1 | Phos-2 | Phos-3 | Phos-4 | Phos-4 | Phos-4 | Phos-4 | Phos-5 | Phos-6 | Phos-6 |
| CF sol'n, ml | 60 | 75 | 75 | 10 | 20 | 20 | 20 | 120 | 20 | 38 |
| NaOH, ml (25% wt) | 15.8 | 14.2 | 13.2 | 1.2 | 0 | 0 | 0 | 21 | 4 | 6 |
| Et3N, ml | 0.72 | 0.68 | 0.9 | 0 | 0 | 0 | 0 | 1.44 | 0 | 0.47 |
| Cyclization Product: | | | | | | | | | | |
| % Cyclics | 70.3 | 83.4 | 89.9 | 93.3 | 87.1 | 88.2 | 80.3 | 82.0 | 88.0 | 76.7 |
| % Polymers | 29.7 | 16.6 | 10.1 | 6.7 | 12.9 | 11.8 | 19.7 | 18.0 | 12.0 | 23.3 |
| Polymr Mw | — | — | — | — | 53,300 | 57,900 | 54,960 | 40,920 | 22,070 | — |
| Mw/Mn | — | — | — | — | 1.47 | 1.42 | 1.50 | 1.41 | 1.35 | — |
| Polymer Fraction: | | | | | | | | | | |
| Carbamates, ppm | — | — | — | — | 983 | 1177 | 1969 | 3239 | 9867 | — |
| Hydroxyl, wt. % | — | — | — | — | 0.0000 | 0.0000 | 0.0000 | 0.0000 | 0.1248 | — |
| % End Groups Accounted For | — | — | — | — | 5.5 | 7.4 | 11.1 | 14.4 | 84.7 | — |
| mol endgroups/mol structural unit in Cyclization Product | | | | | 0.00010 | 0.00011 | 0.00030 | 0.00045 | 0.00320 | — |
| theoretical Mn for Polymerized Cyclics Mixture | | | | | 5,200,000 | 4,700,000 | 1,700,000 | 1,100,000 | 160,000 | — |

Notes: *Comparative BCF Based Cyclics

In CYC-1-3, there is shown that an increase in the weight % of cyclics is favored by decreasing the chloroformate oligomer size used in making such cyclics. CYC-4b-d, and CYC-5 show that the polymer fraction of the monochloroformate cyclization reaction product has unexpectedly low levels of polymer end groups (carbamate and hydroxyl) compared with the polymer fraction of the bischloroformate cyclization (CYC-6a). Accordingly, CYC-4b-d, and CYC-5 (monochloroformate-base cyclic reactions) in principal are capable of making polymer in the 1-5 million number average molecular weight range.

CYC-6A shows that with additional effort for manual pH measurement, high cyclics yield may be obtained from bischloroformate oligomers. However, CYC-6B shows that the cyclics yield can decrease significantly when manual pH measurements for NaOH addition are not performed frequently.

The product of CYC-4d was recovered by allowing the phases to separate and then washing the organic phase with 3N HCl, followed by 3 washes with deionized water. After evaporation of the solvent, the crude cyclics mixture was melt polymerized by submerging a test tube containing the cyclics mixture and 0.05 mol % tetrabutylammonium tetraphenylborate catalyst, under

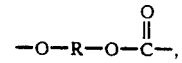

which comprises, (1) simultaneously charging to a reactor,
(A) a composition comprising bisphenol monochloroformate oligomer comprising condensed carbonate units included within the formula,

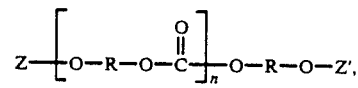

(B) at least one aliphatic or heterocyclic tertiary amine
(C) an aqueous alkali metal hydroxide solution and,
(D) a substantially non-polar organic liquid which forms a two phase system with water, where reagent (A) is charged separately from reagents (B) and (C), (C) is introduced at a rate sufficient to maintain the pH of the reaction mixture at or near a pH set point in the range of between about 10 and 12.5, which reaction mixture in said reactor is subjected to agitation at least sufficient to prevent segregation of the aqueous and organic liquid phases, and (2) recovering the cyclic polycarbonate oligomer from the mixture of (1), where R is a divalent C$_{(6-30)}$ aromatic organic radical, n is an integer having a value of 0 to 40, Z and Z' are either H or

and the —OH and

terminal units of the bisphenol monochloroformate polycarbonate oligomers are present in an amount sufficient to provide an

ratio having a value of from about 0.9 to about 1.1.

2. A method in accordance with claim 1 where R is

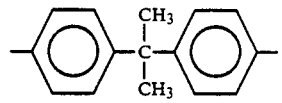

3. A method in accordance with claim 1 where (B) is triethylamine.

4. A method in accordance with claim 1 where (C) is sodium hydroxide.

5. A method in accordance with claim 1 where (D) is methylene chloride.

6. A polycarbonate composition made according to the method of claim 1, comprising cyclic polycarbonate containing less than 0.0001 mol end groups per mol of the structural units, said end groups comprising aromatic hydroxyls and carbonates.

* * * * *